United States Patent
Mustola et al.

(10) Patent No.: US 9,223,930 B2
(45) Date of Patent: Dec. 29, 2015

(54) METHODS AND SYSTEMS FOR IDENTIFYING THE QUANTITATION CYCLE FOR A PCR AMPLIFICATION REACTION

(75) Inventors: Jorma Mustola, Saukkola (FI); Antti Koski, Turku (FI)

(73) Assignee: Thermo Fisher Scientific Oy, Ventaa (FI)

(*) Notice: Subject to any disclaimer, the term of this patent is extended or adjusted under 35 U.S.C. 154(b) by 584 days.

(21) Appl. No.: 13/560,228

(22) Filed: Jul. 27, 2012

(65) Prior Publication Data

US 2013/0030719 A1      Jan. 31, 2013

Related U.S. Application Data

(60) Provisional application No. 61/513,224, filed on Jul. 29, 2011.

(51) Int. Cl.
| | | |
|---|---|---|
| G01N 31/22 | (2006.01) |
| G01N 21/64 | (2006.01) |
| G06F 19/00 | (2011.01) |
| G06F 19/24 | (2011.01) |

(52) U.S. Cl.
CPC ........................................ *G06F 19/24* (2013.01)

(58) Field of Classification Search
CPC ....... G06F 19/24; G06F 19/00; C12Q 1/6851; C12P 19/34; G06K 9/0053; F16L 1/203
USPC ................... 702/19, 30; 435/6.16, 6
See application file for complete search history.

(56) References Cited

U.S. PATENT DOCUMENTS

| | | | |
|---|---|---|---|
| 7,188,030 B2 | 3/2007 | Ward et al. | |
| 7,848,892 B2 | 12/2010 | Ward et al. | |
| 7,856,324 B2 | 12/2010 | Ward et al. | |
| 7,856,325 B2 | 12/2010 | Ward et al. | |
| 2007/0129899 A1* | 6/2007 | Ward et al. | ...................... 702/20 |

OTHER PUBLICATIONS

Lie, Yolanda S., et al., Advances in Quantitative PCR Technology: 5' Nuclease Assays, Current Opinion in Biotechnology, 1998, pp. 43-48, vol. 9.

Heid, Christian A., et al., Real Time Quantitative PCR, Genome Research, 1996, pp. 986-994, vol. 6.

Roche Molecular Biochemicals Technical Note No. LC, Absolute Quantification With External Standards, Nov. 2000, pp. 1-20.

(Continued)

*Primary Examiner* — John H Le
(74) *Attorney, Agent, or Firm* — Wood, Herron & Evans, LLP

(57) ABSTRACT

Methods and systems for identifying a quantitation cycle ($C_q$) for a PCR reaction that includes fitting a line having a plurality of line segments to data points associated with a PCR amplification reaction. The data points include a cycle value associated with a PCR cycle and a product value associated with a PCR product. A baseline is identified and reaction segment associated with an exponential region of the PCR reaction is also identified. The reaction segment includes a subset of the plurality of line segments having a slope not less than a steepness criterion. A reaction line is fit to the data points associated with the reaction segment. The $C_q$ is identified by calculating the cycle value for a data point defining the intersection of the baseline and reaction line.

30 Claims, 8 Drawing Sheets

(56) References Cited

OTHER PUBLICATIONS

Applied Biosystems, User Bulletin #2, ABI Prism 7700 Sequence Detection System, Dec. 11, 1997, pp. 1-36.
Rasmussen, Randy, et al., Quantitative PCR by Continuous Fluorescence Monitoring of a Double Strand DNA Specific Binding Dye, Biochemical, 1998, pp. 8-11, issue 2.
Nitsche, Andreas, et al., Different Real-Time PCR Formats Compared for the Quantitative Detection of Human Cytomegalovirus DNA, Clinical Chemistry, 1999, pp. 1932-1937, vol. 45, issue 11.
Grove, Deborah S., Quantitative Real-Time Polymerase Chain Reaction for the Core Facility Using TaqMan and the Perkin-Elmer/Applied Biosystems Division 7700 Sequence Detector, ABRF, 1999, pp. 1-11.
Giulietti, Annapaula, et al., An Overview of Real-Time Quantitative PCR: Applications to Quantify Cytokine Gene Expression, Methods, 2001, pp. 386-401, vol. 25, Elsevier Science.
Livak, Kenneth J., Analysis of Relative Gene Expression Data Using Real-Time Quantitative PCR and the 2-ΔΔCT Method, Methods, 2001, pp. 402-408, vol. 25, Elsevier Science.
Yajima, Tomomi, et al., Quantitative Reverse Transcription-PCR Assay of the RNA Component of Human Telomerase Using the TaqMan Fluorogenic Detection System, Clinical Chemistry, 1998, pp. 2441-2445, vol. 44, issue 12.
Winer, J., et al., Abstract of Development and Validation of Real-Time Quantitative Reverse Transcriptase-Polymerase Chain Reaction for Monitoring Gene Expression in Cardiac Myocytes in Vitro, Analytical Biochemistry, May 1999, pp. 41-49, vol. 270, No. 1, Academic Press.
Freeman, Willard M., et al., Quantitative RT-PCR: Pitfalls and Potential, BioTechniques, Jan. 1999, pp. 112-125, vol. 26, No. 1.
Bustin, S. A., Absolute Quantification of mRNA Using Real-Time Reverse Transcription Polymerase Chain Reaction Assays, Journal of Molecular Endocrinology, 2000, pp. 169-193, vol. 25.
Saraswathy, T.S., et al., Abstract of Human Immunodeficiency Virus Type 1 Subtypes Among Malaysian Intravenous Drug Users, Southeast Asian J Trop Med Public Health, Jun. 2000, pp. 283-286, vol. 31, issue 2.
Rostaing, L., et al., Abstract of Changes in Hepatitis C Virus RNA Viremia Concentrations in Long-Term Renal Transplant Patients After Introduction of Mycophenolate Mofetil, Transplantation, Mar. 2000, pp. 991-994, vol. 16, issue 69.
Morin, et al., Laboratory for Conservation Genetics, Leipzig, Molecular Ecology, 2001, pp. 1835-1844, vol. 10, www.rareDNA.com.
Alexanderson, S., Abstract of the Early Pathogenesis of Foot-and-Mouth Disease in Pigs Infected by Contact: A Quantitative Time-Course Study Using TaqMan RT-PCR, J Gen Virol, Apr. 2001, pp. 747-755, vol. 82, part 4.
Levis, J., et al., Abstract of Strategy for the Maximization of Clinically Relevant Information From Hepatitis C Virus, RT-PCR Quantification, J Clin Virol, Feb. 2001, pp. 163-171, vol. 20, issue 3.
Pfaffl, Michael W., A New Mathematical Model for Relative Quantification in Real-Time RT-PCT, Nucleic Acids Research, 2001, p. e45, vol. 29, No. 9, Oxford University Press.
Bustin, S. A., Quantification of mRNA Using Real-Time Reverse Transcription PCR (RT-PCR): Trends and Problems, Journal of Molecular Endocrinology, 2002, pp. 23-39, vol. 29.
Ginzinger, David G., Gene Quantification Using Real-Time Quantitative PCR: An Emerging Technology Hits the Mainstream, Experimental Hematology, 2002, pp. 503-512, vol. 30, Elsevier Science.
Morrison, Tom, et al., Nanoliter High Throughput Quantitative PCR, Nucleic Acids Research, 2006, pp. 1-9 and e123, vol. 34, No. 18, The Authors.
Roche, LightCycler, Roche Applied Science Technical Note No. LC 13/2001 (28 total pages).
Higuchi, Russell, et al., Kinetic PCR Analysis: Real-Time Monitoring of DNA Amplification Reactions, Bio/Technology, Sep. 1993, pp. 1026-1030, vol. 11.
U.S. Appl. No. 60/313,882, filed Aug. 21, 2001 (68 pages total).
Applied Biosystems, Data Analysis on the ABI Prism 7700, Sequence Detection System: Setting Baselines and Thresholds, pp. 1-12 (2002).
Peccoud, Jean et al., Statistical Estimations of PCR Amplification Rates, Gene Quantification, published by F. Ferrë, Ed., (New York Birhhauser), pp. 111-123, pp. 1-17 (Jan. 1, 1998).

\* cited by examiner

METHODS AND SYSTEMS FOR IDENTIFYING THE QUANTITATION CYCLE FOR A PCR AMPLIFICATION REACTION

CROSS-REFERENCE TO RELATED APPLICATIONS

This application claims the benefit of and priority to prior filed Provisional Application Ser. No. 61/513,224, filed Jul. 29, 2011, which is expressly incorporated herein by reference.

BACKGROUND

The invention relates generally to methods and systems for analyzing data from a Polymerase Chain Reaction (PCR) amplification reaction, and more particularly to methods and systems for identifying the quantitation cycle ($C_q$) for a PCR amplification reaction.

PCR is a powerful technique used to amplify genetic material. Quantitative PCR (q-PCR) is a technique used to quantify the amount of a targeted genetic material initially present in a sample. For example, under certain conditions, a cell may alter its expression of a target gene. Q-PCR allows a researcher to quantify the effect of different conditions on the expression of a target gene.

Q-PCR techniques rely on some method of detecting a change in the quantity of a PCR product over the course of a multitude of PCR cycles. Q-PCR techniques generally utilize fluorescent probes that increase in fluorescence relative to the amount of PCR product produced during each amplification cycle. Detecting fluorescence attributable the PCR product is complicated by the presence of background fluorescence in the PCR reaction chamber. Thus, an important factor affecting the accuracy and reproducibility of q-PCR data is identifying the amplification cycle wherein the fluorescent signal attributable to the amplification of the PCR product is detectable above background fluorescent signal.

To this end, conventional q-PCR analytical techniques first identify a threshold fluorescence value, which is then used to identify the $C_q$. The threshold value is a minimum fluorescence signal value wherein the fluorescence signal is attributable to the amplification of the PCR product. The $C_q$ is then identified as the PCR cycle where the fluorescence from the amplified PCR product is greater than the threshold value.

A variety of conventionally methods for identifying the threshold value are available. For example, in one method, the average fluorescence of a background region is added to a multiple of the standard deviation for the average fluorescence of the background region of a PCR amplification plot. Other methods use complex algorithms and statistical analyses of the amplification data to identify the threshold. These indirect methods of identifying the $C_q$ based on the threshold can yield variable and inaccurate results that are difficult to reproduce.

However, methods and systems of directly identifying the $C_q$ for data from a PCR amplification reaction that do not rely on identifying a threshold value are needed.

BRIEF SUMMARY

Described herein are methods and systems for identifying a $C_q$ for a PCR amplification reaction that includes fitting a line having a plurality of line segments to data points associated with a PCR amplification reaction. The data points include a cycle value associated with a PCR cycle and a product value associated with a PCR product. The methods and systems further include identifying a baseline and a reaction line associated with the PCR amplification reaction. The reaction line is based on a subset of line segments from the plurality of line segments that have a slope not less than a steepness criterion. The $C_q$ is identified by calculating the cycle value for a data point defining the intersection of the baseline and the reaction line.

BRIEF DESCRIPTION OF THE SEVERAL VIEWS OF THE DRAWINGS

The accompanying drawings, which are incorporated in and constitute a part of this specification, illustrate various embodiments of the invention and, together with a general description of the invention given above and the detailed description of the embodiments given below, serve to explain the embodiments of the invention.

DETAILED DESCRIPTION

Figure 1:
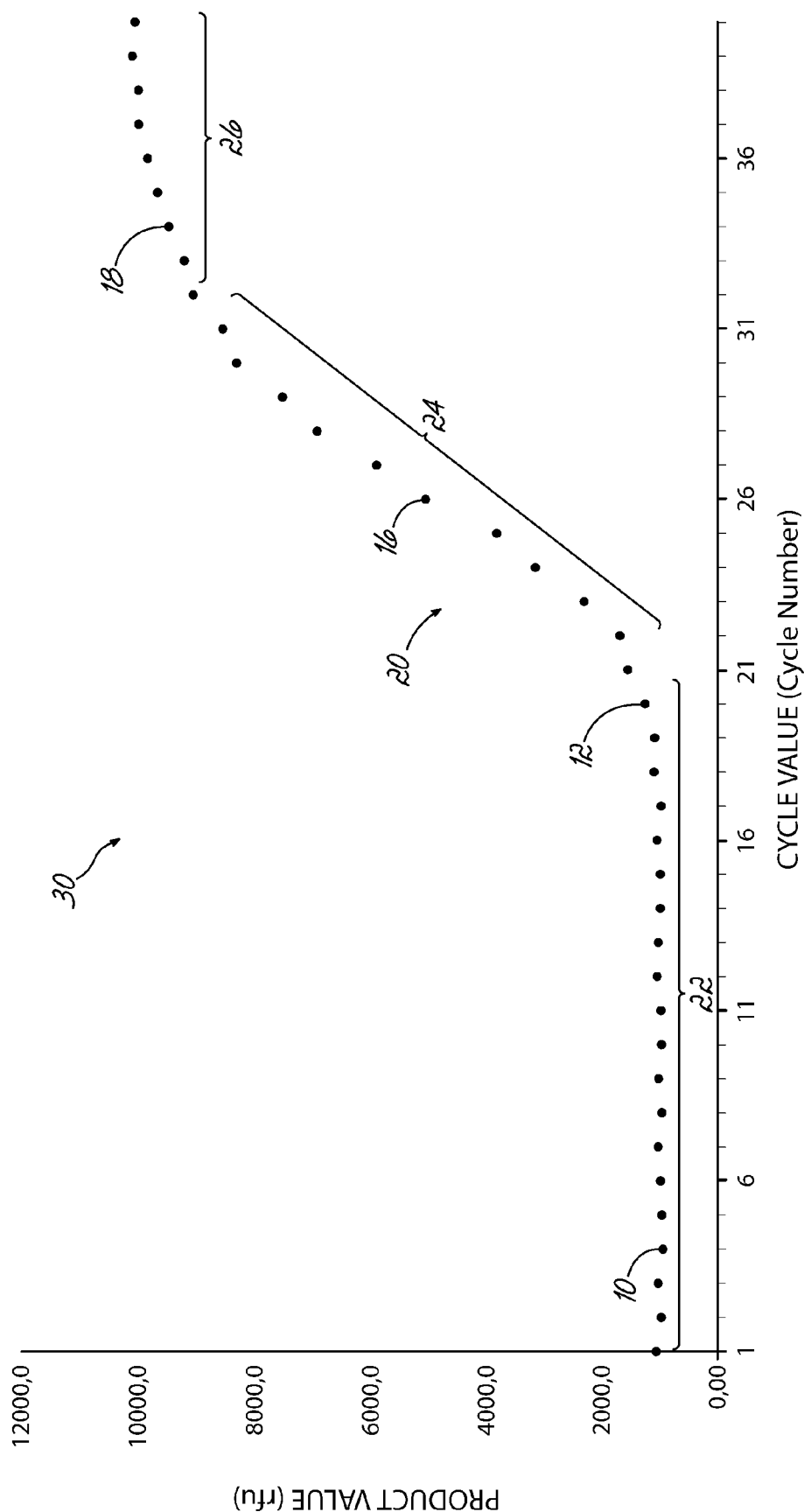
FIG. 1 is a graph illustrating an exemplary PCR amplification plot of data from a PCR reaction.

With reference to FIG. 1, and in accordance with embodiments of the invention, an improved method of identifying the $C_q$ from PCR reaction data includes analyzing data collected from a q-PCR reaction that is characterized by a plurality of data points 10, 12, 16, and 18 (x-axis) each including a cycle value representative of the PCR cycle for which the data point was obtained, and a product value representative of the PCR product (y-axis). In an exemplary embodiment of the invention, the cycle value is expressed as the PCR cycle and the product value is expressed as relative fluorescent units (rfu's).

The data points 10, 12, 16, 18 (FIG. 1) for a q-PCR reaction generally form a sigmoid shaped curve 20 having a background region 22, an amplification region 24, and a plateau region 26. The background region 22 is a relatively flat region typically at early cycle values in the curve 20 and characterized by low product values because the product value, such as a fluorescent signal, generated by the amplification of the PCR product is not sufficient to overcome the background signals in the reaction chamber. The amplification region 24 is a central region of the curve 20 wherein the product value, such as a fluorescent signal, generated by the PCR product is sufficient to overcome the background signal in the reaction chamber and the product value increases in an exponential manner from one cycle value to the next. The plateau region 26 is a relatively flat region typically at later cycle values in the curve 20 and for which the reactant concentrations are no longer sufficient to maintain the exponential increase in the product values observed in the amplification region 24. It is noted that while the sigmoid shaped curve 20 in FIG. 1 is ascending, the data could be collected in a format wherein the sigmoid shaped curve is descending (not shown).

Figure 2:
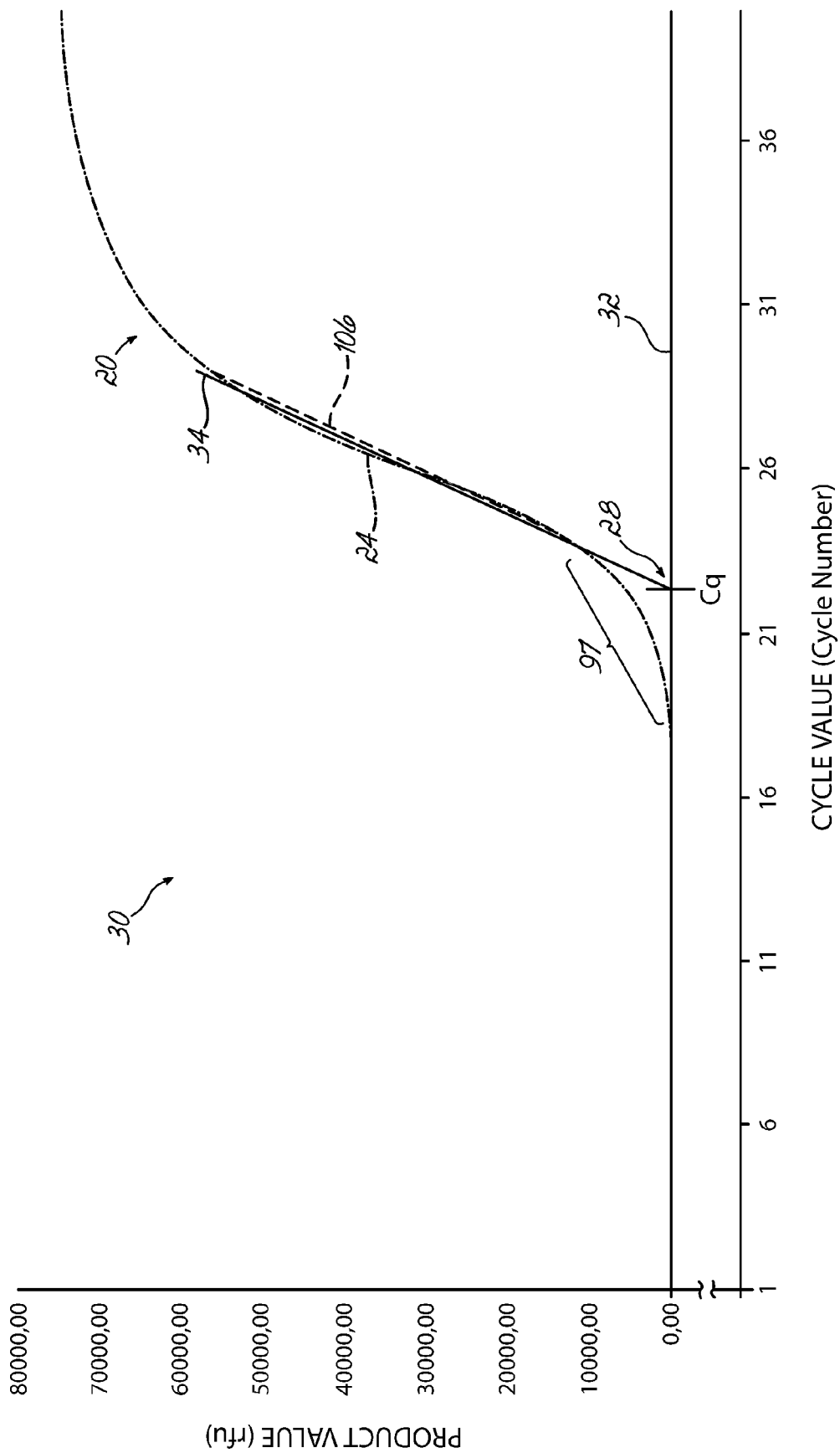
FIG. 2 is a graph illustrating the identification of the $C_q$ in accordance with embodiments of the invention.

With reference to FIGS. 2 to 10 in which like reference numerals refer to like features, embodiments of the invention identify the $C_q$ for a PCR amplification reaction. In contrast to routine methods of identifying a $C_q$ for a PCR reaction that indirectly identify the $C_q$ by first identifying a threshold value, embodiments of the invention directly calculate the $C_q$ 28 from the PCR reaction data 30 without first having to identify a threshold value. This method is referred to herein as the "direct method" 31 and 31' of FIGS. 3 and 4, respectively. As illustrated in FIG. 2, the amplification region 24 of the PCR reaction data 30 is analyzed to identify a baseline 32 and a reaction line 34 and the $C_q$ 28 is calculated as the cycle value wherein the reaction line 34 intersects the baseline 32.

Figure 3:
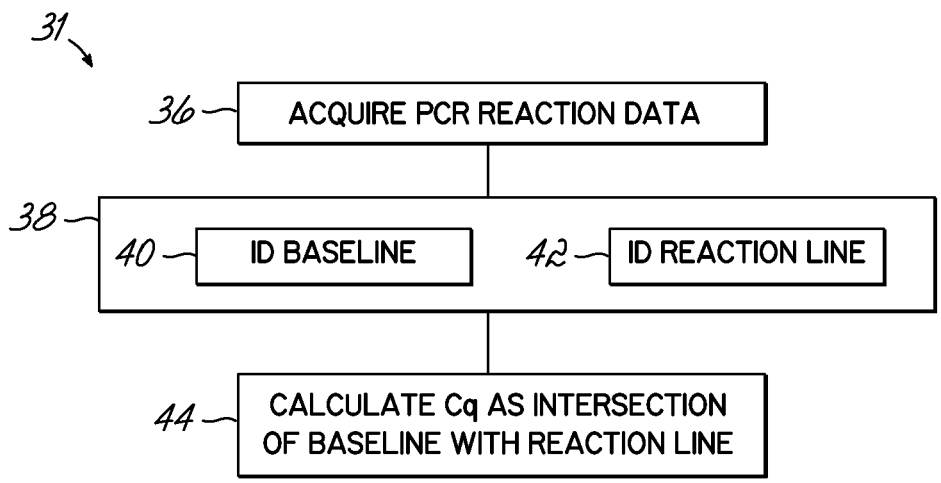
FIG. 3 is a flow chart illustrating the process of identifying a $C_q$ in accordance with embodiments of the invention.
Figure 4:
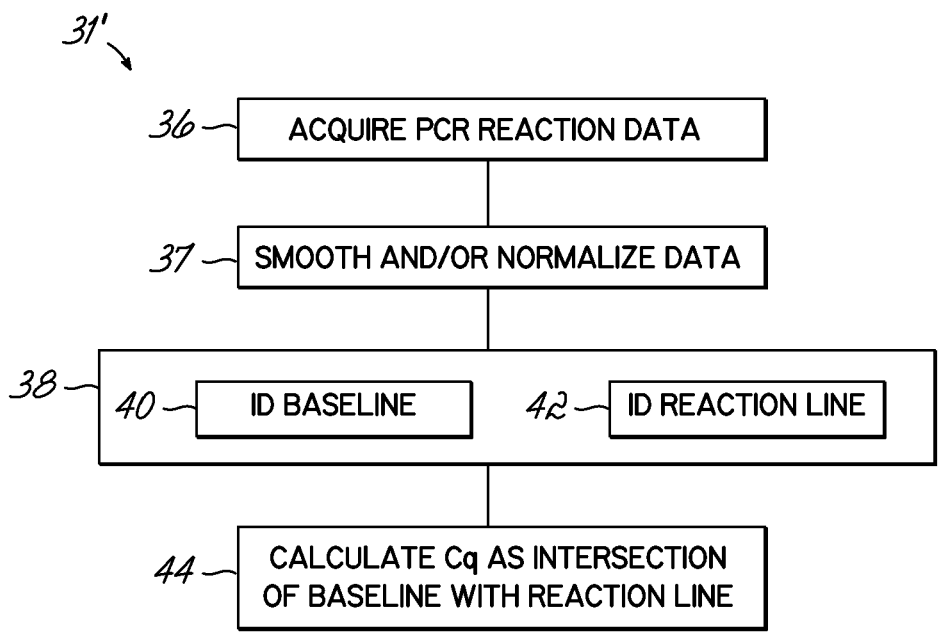
FIG. 4 is a flow chart illustrating the process of identifying a $C_q$ in accordance with embodiments of the invention.

FIGS. 3 and 4 illustrate embodiments of the direct method of identifying the $C_q$ 28 that include acquiring PCR reaction data (block 36) and analyzing the data (block 38) to identify a baseline (block 40) and a reaction line (block 42) and calculating the $C_q$ as the intersection of the baseline with reaction line (block 44). In some embodiments and as shown by method 31' in FIG. 4, the PCR reaction data 30 are internally smoothed and/or normalized (block 37) prior to analyzing the data (block 38) to identify the baseline (block 40) and the reaction line (block 42).

The internally smoothing process may employ any process that internally smoothes the data. For example, in one embodiment, the smoothing process employs a rolling average method that averages the product values for a plurality of consecutive data points from the PCR reaction data. In another embodiment, the data are smoothed with a Savitzky-Golay smoothing filter by fitting an $n^{th}$ degree polynome to a plurality of consecutive data points and calculating a smoothed product value for one or several data points with the plurality of data points. In one embodiment, the user may optionally designate the number of data points used for the rolling average.

The normalizing process may employ any process that normalizes the data. For example in one embodiment, the normalizing process assigns a first normalized product value to the data point having the lowest product value and a second normalized product value to the data point having the highest product value. The remaining data points are normalized relative to the first normalized product value and the second normalized product value. In one embodiment, the data are normalized between about 1,000 RFU and about 10,000 RFU.

Figure 5:
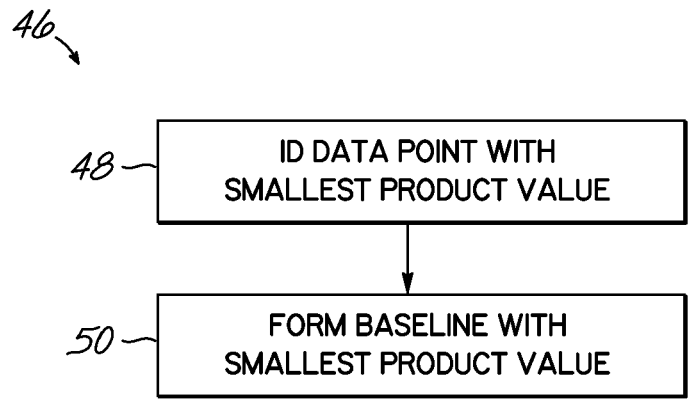
FIG. 5 is a flow chart illustrating a process of identifying a baseline in accordance with embodiments of the invention.
Figure 6:
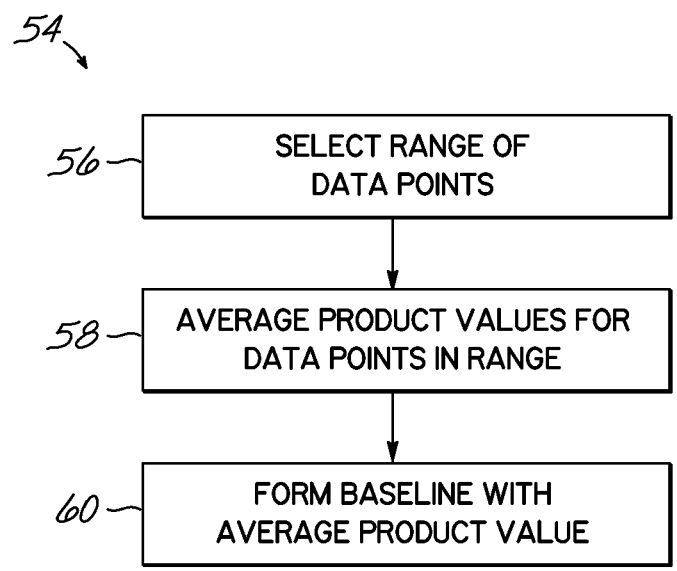
FIG. 6 is a flow chart illustrating a process of identifying a baseline in accordance with embodiments of the invention.
Figure 7:
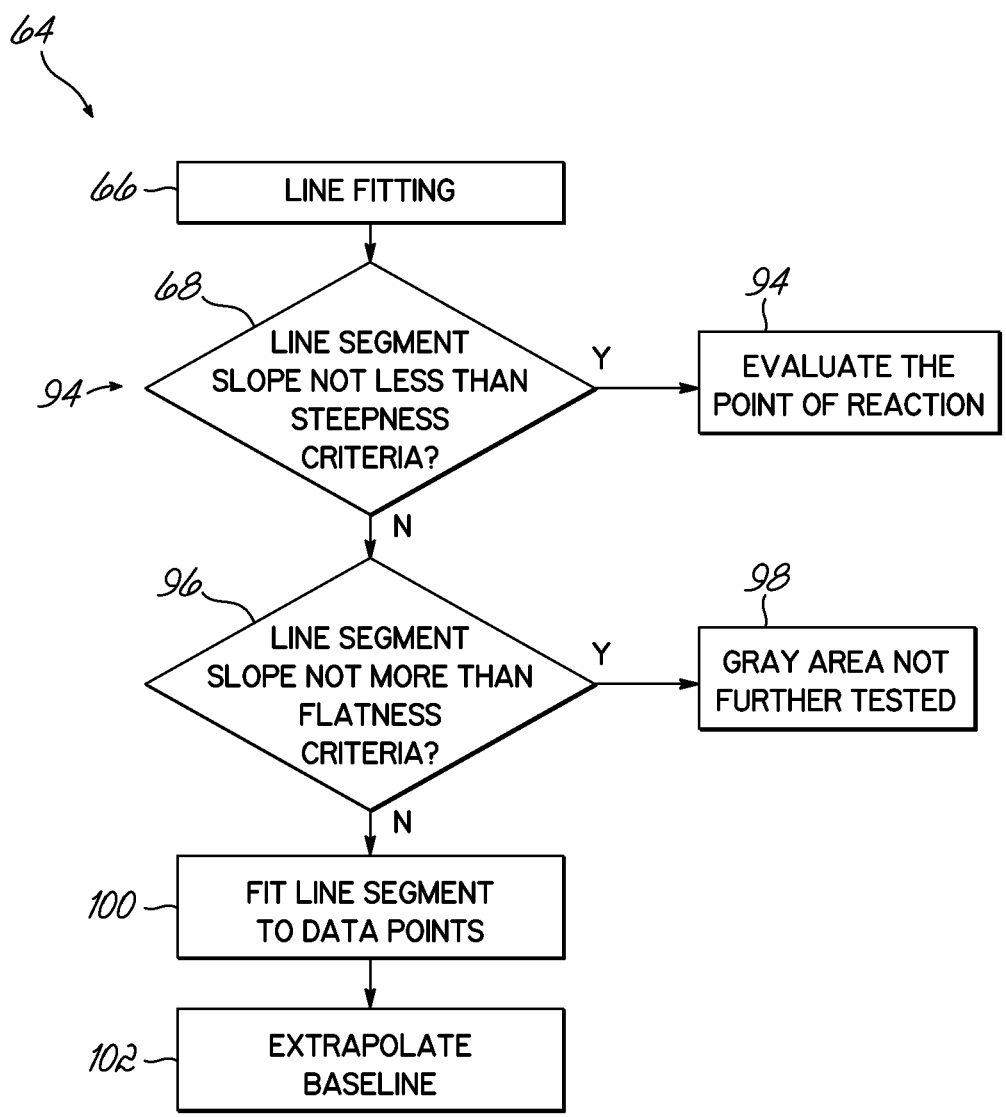
FIG. 7 is a flow chart illustrating a process of identifying a baseline in accordance with embodiments of the invention.

Any method for identifying and/or optionally removing a baseline (block 40) may be employed, such as the curve minimum method 46 in FIG. 5, the cycle range method 54 in FIG. 6, or the automatic trend method 64 of FIG. 7. The term "baseline" is understood to include lines and line segments, as well as product values that may be used in accordance with the invention. For example, the baseline need not be separately identified, but could be identified as a product value that can be applied to the PCR reaction data such as by subtraction from the product values of the data points from a PCR reaction.

For the curve minimum method 46, a value associated with the smallest product value from any data point obtained from a PCR reaction is identified (block 48) and the baseline is formed with the value associated with the smallest product value (block 50). In one embodiment, the value associated with the smallest product value is the smallest product value. It is not necessary to separately define a baseline with this method. For example, the value associated with the smallest product value may be subtracted from the product values for all of the data points from the PCR amplification reaction so that the x-axis of a plot of the data points functions as the baseline. Alternatively, a baseline may be separately defined wherein all of the data points in the baseline will have the same product value as the value associated with the smallest product value in the PCR reaction data.

For the cycle range method 54, a range of data points are selected (block 56), the product values for data points in a selected range are averaged (block 58), and a baseline is formed with a value associated with the average product value from the range (block 60). Non-limiting exemplary methods of selecting the range of data points include user selection, default selection employing a set cycle value range, or a selection based on an analysis of the data from the PCR reaction. The range of data points generally corresponds with data points in the background region 22 (FIG. 1). Like the curve minimum method 46, it is not necessary to separately define the baseline with the cycle range method 54. For example, the value associated with the average product value may be subtracted from the product values for all of the data points from the PCR reaction so that the x-axis of a plot of the data points functions as the baseline. Alternatively, a baseline may be separately defined wherein all of the data points in the baseline will have the same product value as the value associated with the average product value of the data points in the selected range.

Figure 8:
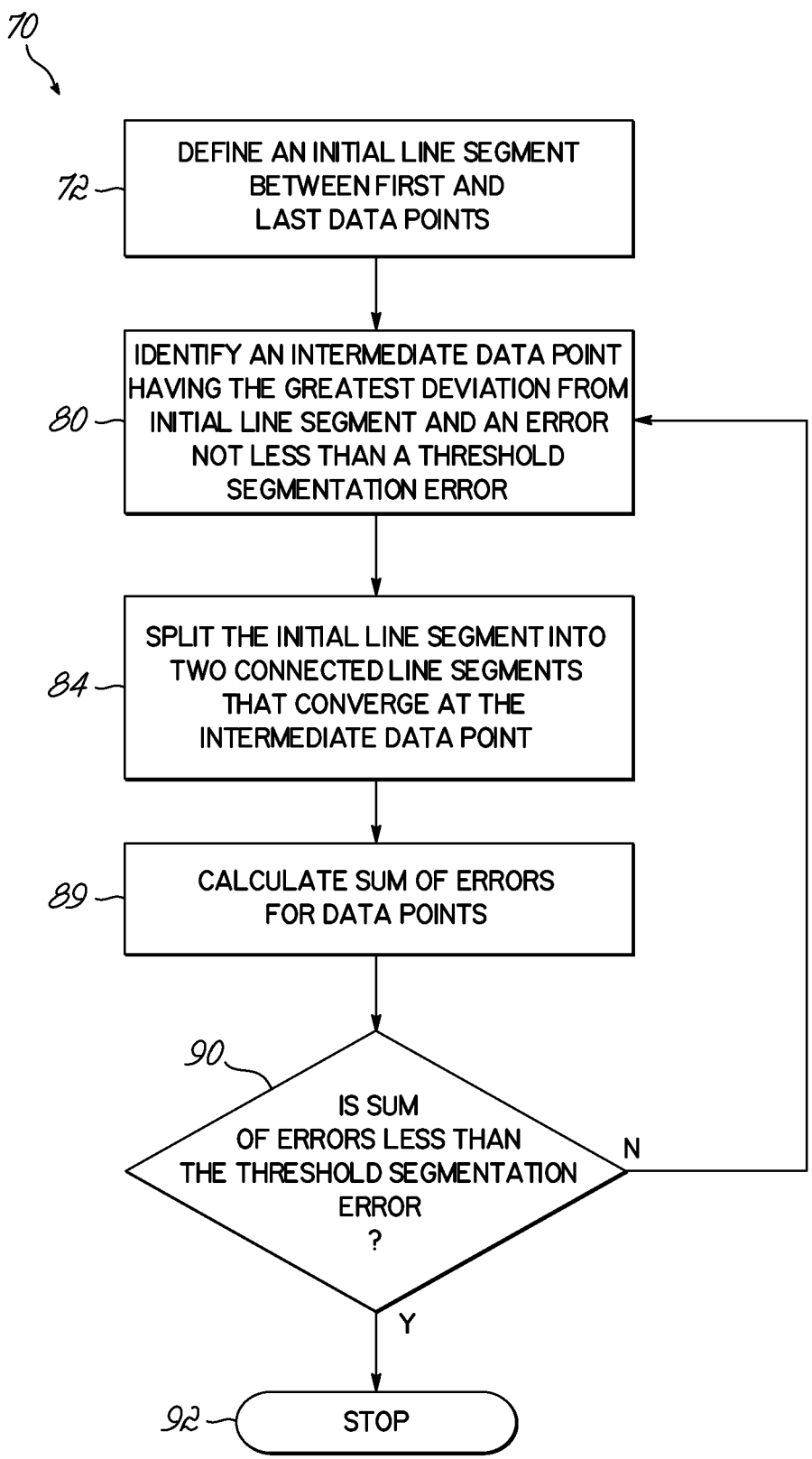
FIG. 8 is a flow chart illustrating a process of fitting a line to a PCR reaction data in accordance with embodiments of the invention.
Figure 9:
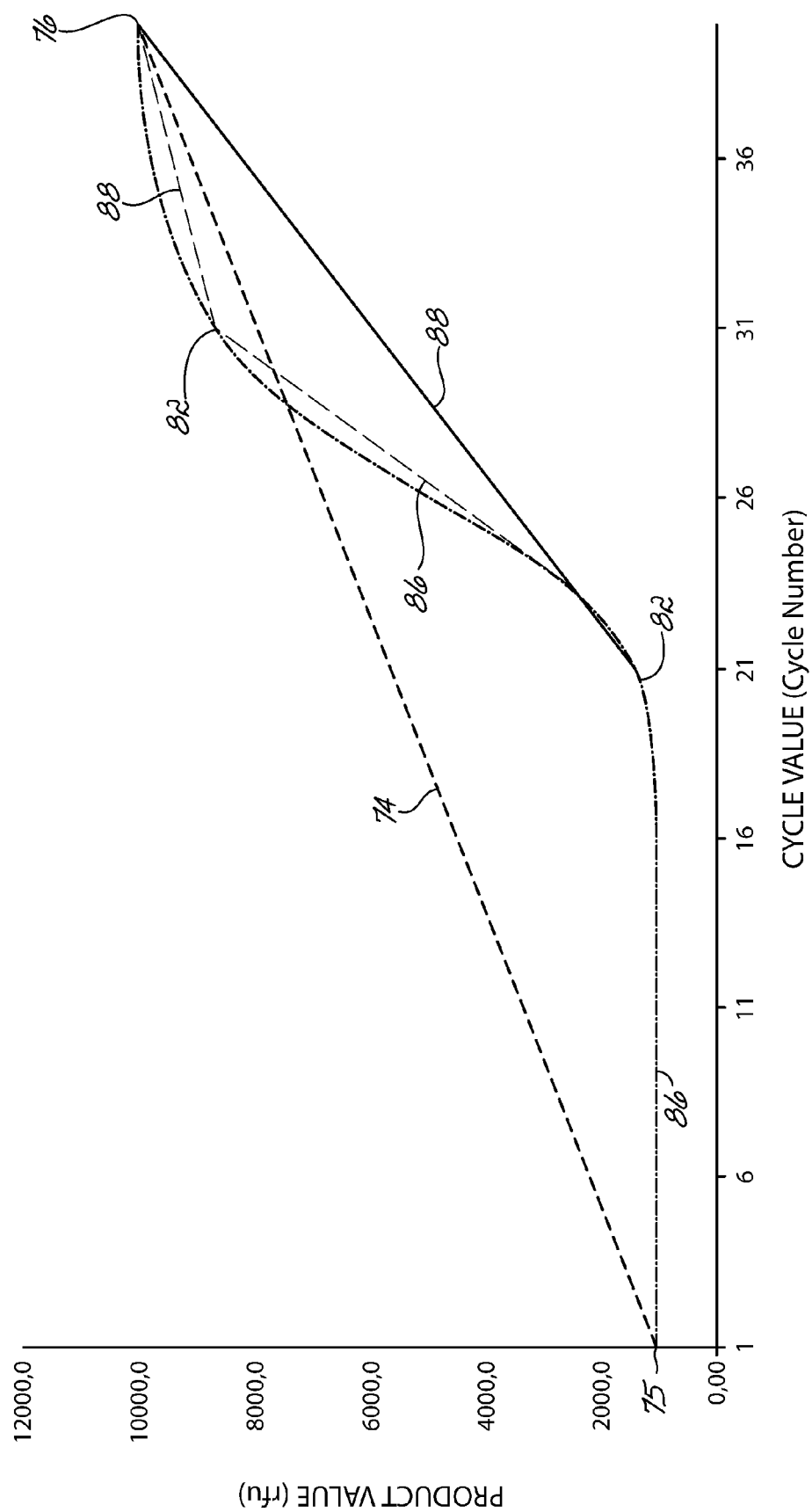
FIG. 9 is graph illustrating a process of fitting a line to a PCR reaction data in accordance with embodiments of the invention.
Figure 10:
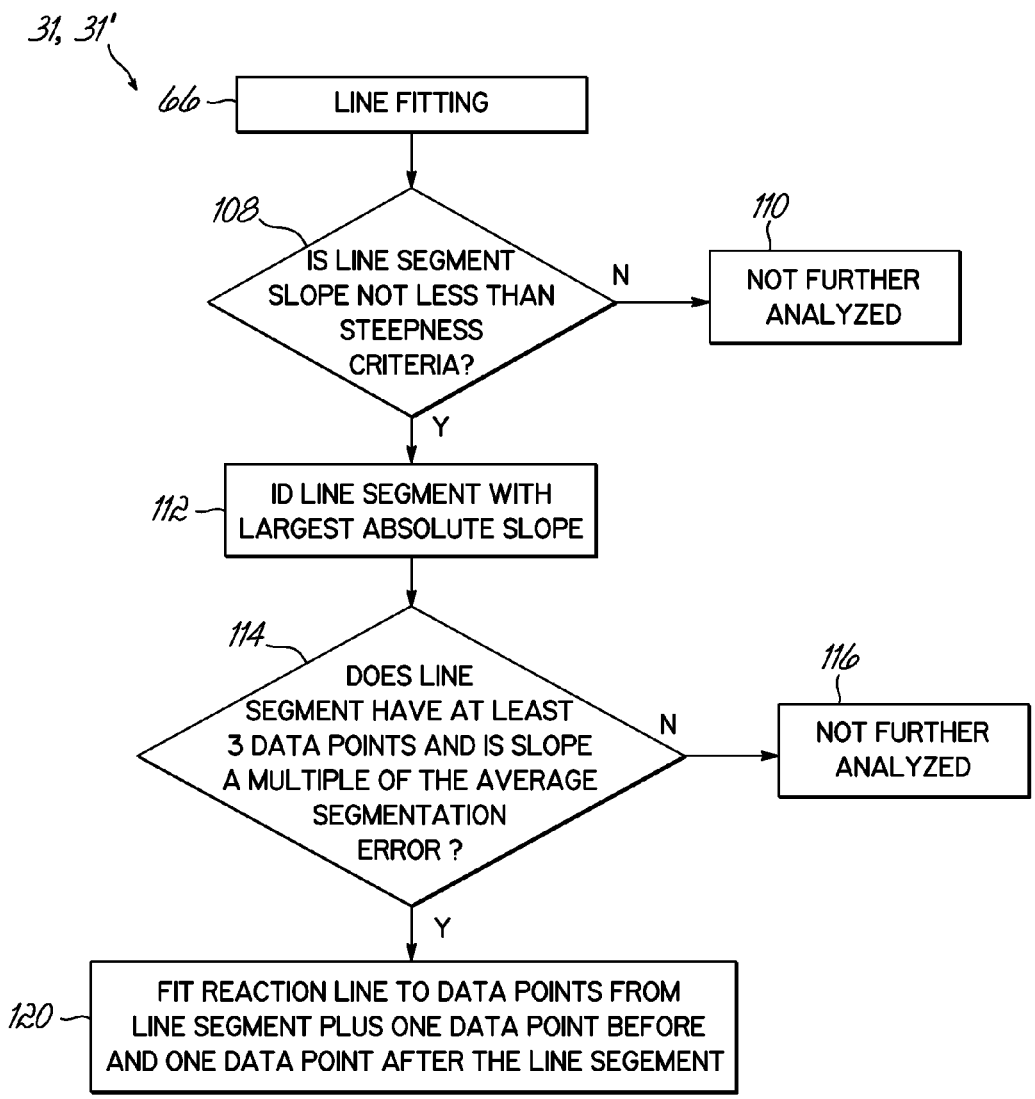
FIG. 10 is a flow chart illustrating a process of identifying a reaction line in accordance with embodiments of the invention.
Figure 11:
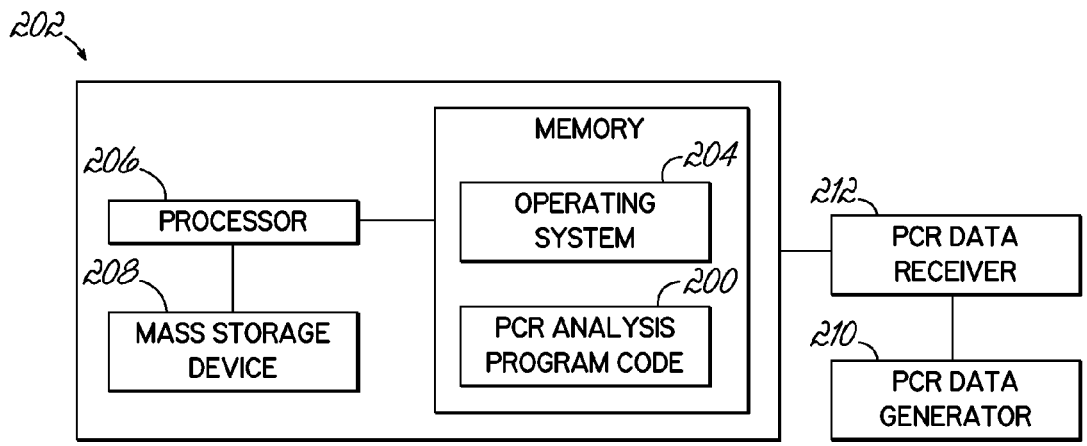
FIG. 11 is a block diagram of a computer system in accordance with embodiments of the invention.

For the automatic trend method 64, an algorithm identifies a baseline for the PCR reaction data 30 (FIG. 1). As shown in FIG. 7, the first step in the process includes fitting a line (block 66) comprising a connected series of line segments to the PCR reaction data 30 in a piecewise continuous linear curve. In one embodiment, the PCR reaction data 30 is fit using a polyline segmentation method 70 as illustrated in FIGS. 8 and 9. The polyline segmentation method 70 is conducted by defining (block 72) an initial line segment 74 (FIG. 9) between the data point at the initial cycle value 75 (FIG. 9) and the data point associated with the last cycle value 76 (FIG. 9), identifying (block 80) an intermediate data point 82 (FIG. 9) having the greatest deviation in the product value relative to the initial line segment 74, and then splitting (block 84) the initial line segment into two connected line segments 86 and 88 (FIG. 9) that converge at the intermediate data point 82 (FIG. 9). The sum of errors for at least a portion of the data points, and in some embodiments, all of the data points, in the PCR amplification reaction is then calculated (block 89). This process is repeated for each of the line segments until the sum of errors for the data points in the PCR amplification reaction is less than the threshold segmentation error (blocks 90 and 92). In one embodiment, the threshold segmentation error is about 1.5% of the sum of the product values.

With renewed reference to FIG. 7, after fitting the piecewise continuous linear curve (block 66) to the PCR reaction data, the next step is the identification of the baseline area. In one embodiment, the first step in identifying the baseline area is identifying the point of the reaction (block 94), which is the line segment with the largest absolute slope, i.e., the largest group of similarly ascending (or descending) line segments having the greatest steepness. To identify the point of the reaction (block 94), the line segments from the piecewise continuous linear curve are divided into groups of consecutive segments that are all either ascending or descending. The absolute value of the slopes of these segments must be greater than the steepness criterion in order to be analyzed for the reaction segment (block 68). In one embodiment, the steepness criterion is calculated with the formula:

$$\text{Steepness criterion} = \mu + C_1 \times \sigma$$

wherein $\mu$ is the average absolute slope of all the line segments, $C_1$ is the steepness constant, and $\sigma$ is the standard deviation of the absolute slopes of all of the line segments. In one embodiment, the $C_1$ is about 0.65. One skilled in the art will appreciate that other values and/or factors could be employed for calculating the steepness criterion.

From this group of line segments, the line segments having the largest absolute product value change are selected as the reaction group. The reaction segment is the line segment with the largest absolute slope in the reaction group. If the reaction segment has at least three data points and a slope greater than a steepness criterion and the slope of the reaction segment is greater than a multiple of the average segmentation error, then the reaction segment represents the point of the reaction (block 94). In one embodiment, the multiple of the segmentation is 20 times the average segmentation error. In another embodiment, the multiple of the segmentation is 40 times the average segmentation error.

After identifying the point of the reaction (block 94), a baseline region is identified as the longest consecutive subset of the line segments before the reaction segment having a slope not more than a flatness criterion (block 96). In one embodiment, the flatness criterion is calculated with the formula:

$$\text{flatness criterion} = \mu - C_2 \times \sigma$$

wherein $\mu$ is the average absolute slope of all the line segments, $C2$ is the flatness constant, and $\sigma$ is the standard deviation of the absolute slopes of all of the line segments. In one embodiment, $C_2$ is about 0.5. One skilled in the art will appreciate that other values and/or factors could be employed for calculating the flatness criterion.

Line segments having a slope less than the steepness criterion but greater than the flatness criterion fall into a gray area 97 (FIG. 2) that is not further analyzed (block 98).

Next, a line is fit by linear regression (block 100) to the data points associated with the baseline region 22 (FIG. 2) to form a baseline segment, which is extrapolated (block 102) to form the baseline 32 (FIG. 2). The baseline 32 can be used to identify product values for each cycle value that can be removed from each data point in the PCR reaction data 30, or separately defined as a baseline 32.

After the identification and optional removal of the baseline 32, the $C_q$ 28 (FIG. 2) is calculated with the direct method 31, 31' (FIGS. 3 and 4). For the direct method 31, 31' the PCR reaction data 30 are analyzed using a process similar to process described to identify the baseline with the automatic trend baseline method, that is a piecewise continuous linear curve 66 is fit to the PCR reaction data 30 (FIG. 1) and the reaction line 34 (FIG. 2) is identified by the approach in FIG. 10. The reaction segment is identified (block 108) by determining if the slope of any line segment is not less than the steepness criterion as defined above. If the slope is less than the steepness criterion, then the line segments are not further analyzed (block 110). For line segments wherein the slope is not less than the steepness criterion, the line segment with the largest absolute slope (block 112) is identified based on a reaction segment 106 (FIG. 2). In embodiments that remove the baseline 32, the alteration of the data caused by the baseline removal could result in the identification of additional line segments having a slope that is not less than the steepness criterion and which could be identified as the reaction segment 106.

The piecewise continuous linear curve 66 may be fit to the PCR reaction data 30 using the poly line segmentation method described above and illustrated in FIGS. 8 and 9. If the line segment with the largest absolute slope has a minimum number of data points, such as at least three data points, and the product value change is at least greater than some multiple of the average segmentation error, such as greater than about 20 times the average segmentation error (block 114), the line segment is identified as the reaction segment 106 (FIG. 2). If the line segment fails (block 116) to meet the criteria, then no reaction is detected and the direct method may not be used to identify the $C_q$. Next, the reaction line 34 (FIG. 2) is fit (block 120, FIG. 10) to the data points encompassed by the reaction segment 106. In one embodiment, the reaction line 34 is fit by linear regression to the data points in the reaction segment 106 plus one or more data points from cycles before and/or after the reaction segment 106, such as one cycle value before the reaction segment 106 and/or one cycle value after the reaction segment 106. Thus, the reaction line 34 may be based on a slightly enlarged set of data points than originally identified with the reaction segment 106 to eliminate the inaccuracies of the line segmentation method 70. The $C_q$ 28 (FIG. 2) is the value at which the reaction line 34 intersects the baseline 32. For the purpose of identifying the $C_q$ 28, the baseline 32 can be the actual baseline calculated as described above, or if the calculated baseline cycle value has been removed from the cycle values for the data points, the x-axis will serve as the baseline. It is noted that the baseline can be identified and/or removed using any baseline identification and removal techniques such as those described herein.

Individual Cq's identified for individual PCR reactions may be combined to calculate a combined $C_q$. For example, individual $C_q$'s for two or more PCR reactions may be combined by averaging the individual $C_q$'s.

Those skilled in the art will appreciate that the identification of the baseline and reaction line may be conducted in single step, such as through the combination of automatic trend baseline method and the direct $C_q$ method. It will further be appreciated that the reaction line may be identified before, after, and/or simultaneous with the identification of the baseline. The analytical processes of the invention may be embodied as a method, a computer program product that includes program code 200 to execute the method, and/or a computer system 202 configured to execute the method. The method includes the steps described herein and illustrated in FIGS. 1 to 10 for analyzing PCR reaction data to identify a $C_q$.

The program code 200 includes instructions executable on a computer system for carrying out the steps of the method. In one embodiment, the program code 200 includes instructions for identifying a $C_q$ based on PCR reaction data. Embodiments of the invention, whether implemented as part of an operating system 204, application, component, program code 200, object, module or sequence of instructions executed by one or more processing units 206 are referred to herein as "program code." The program code 200 typically comprises one or more instructions that are resident at various times in various memory 202 and storage devices 208 in the computer system 200 that, when read and executed by one or more processors 204 thereof cause that computer system 200 to perform the steps necessary to execute the instructions embodied in the program code 200 embodying the various aspects of the invention.

While embodiments of the invention are described in the context of fully functioning computing systems 200, those skilled in the art will appreciate that the various embodiments of the invention are capable of being distributed as a program product on a computer readable storage medium. The program product may embody a variety of forms. The invention applies equally regardless of the particular type of computer readable storage medium used to actually carry out the distribution of the program code 200. Examples of appropriate computer readable storage media for the program product include, but are not limited to, non-transitory recordable type media such as volatile and nonvolatile memory devices, floppy and other removable disks, hard disk drives, USB drives, optical disks (e.g. CD-ROM's, DVD's, Blu-Ray discs, etc.), among others.

Any of the individual processes described above or illustrated in FIGS. 1-10 may be formed into routines, procedures, methods, modules, objects, and the like, as is well known in the art. It should be appreciated that embodiments of the invention are not limited to the specific organization and allocation of program functionality described herein.

In addition, the systems for analyzing PCR data may further include a module for collecting the PCR reaction data (i.e. a PCR data generator) 210 and a module for receiving PCR reaction data 212. The PCR reaction data collection module may include a thermocycler and a device for detecting the product value that result from a PCR amplification reaction, such as a change in fluorescence in the PCR amplification reaction chamber. PCR data collection modules as known in the art may be used in accordance with the invention. The PCR reaction data receiving module includes components and/or program code to receive PCR reaction data from the PCR reaction data collection module.

While the present invention has been illustrated by the description of specific embodiments thereof, and while the embodiments have been described in considerable detail, it is not intended to restrict or in any way limit the scope of the appended claims to such detail. The various features discussed herein may be used alone or in any combination. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of the general inventive concept.

What is claimed is:

1. A method of identifying a quantitation cycle ($C_q$) for a Polymerase Chain Reaction (PCR) amplification reaction characterized by a plurality of data points each including a cycle value associated with a PCR cycle and a product value associated with a PCR product, the method comprising:
   a) fitting a plurality of line segments to the data points associated with the PCR amplification reaction;
   b) identifying, using a processor, a baseline of the PCR amplification reaction;
   c) identifying a reaction segment associated with an exponential region of the PCR amplification reaction as a first subset of the plurality of line segments having a slope not less than a steepness criteria;
   d) fitting a reaction line to the data points associated with the reaction segment; and
   e) extrapolating the reaction line to intersect the baseline at the $C_q$.

2. The method of claim 1 wherein the first value is a cycle number and the second value is a relative fluorescent unit.

3. The method of claim 1 wherein the line segments are fit to the data points associated with the PCR amplification reaction using a polyline segmentation procedure.

4. The method of claim 3 wherein the polyline segmentation procedure comprises:
   a) defining a temporary line segment between the data point at the initial cycle value and the data point associated with the last cycle value;
   b) identifying one of the data points having a greatest deviation in the product value relative to the temporary line segment;
   c) splitting the temporary line segment to pass through the one of the data points;
   d) calculating the sum of errors for data points in the PCR amplification reaction; and
   e) repeating steps b), c), and d) with the split line segments until the sum of errors for the data points in the PCR amplification reaction is less than the threshold segmentation error.

5. The method of claim 1 further comprising:
   assigning a first normalized product value to the data point having a lowest product value;
   assigning a second normalized product value to the data point having a highest product value; and
   before fitting the line segments to the data points associated with the PCR amplification reaction, normalizing the product values for the remaining data points relative to the first normalized product value and the second normalized product value.

6. The method of claim 5 wherein the first normalized product value is 1,000 rfu and the second normalized product value is 10,000 rfu.

7. The method of claim 5 further comprising converting the product values for the data points back to the original values prior to one of step b) or step c).

8. The method of claim 5 further comprising:
   internally smoothing the data points prior to normalizing the product values for the remaining data points.

9. The method of claim 8 wherein internally smoothing the data points comprises averaging the product values for a plurality of consecutive data points.

10. The method of claim 9 wherein the plurality of consecutive data points ranges from three data points to seven data points.

11. The method of claim 8 wherein internally smoothing the data points comprises:
    fitting a n-th degree polynome to a plurality of consecutive data points and calculating a smoothed product value for one or several data points with the plurality of data points.

12. The method of claim 8 further comprising:
    converting the product values for the data points back to the original values prior to step b) or step c).

13. The method of claim 1 wherein step b) is performed after step c) or after step d).

14. The method of claim 1 wherein identifying the baseline of the PCR amplification reaction comprises:
    subtracting the product values for the baseline from the data points.

15. The method of claim 14 wherein the product values for the baseline are one of a value associated with the lowest product value for any data point associated with PCR amplification reaction or a value associated with the average product value for a subset of data points selected by a user, or a product value selected by the user.

16. The method of claim 1 wherein identifying the baseline of the PCR amplification reaction comprises:

a) identifying a baseline region associated with the PCR amplification reaction wherein the baseline region includes the longest consecutive subset of the plurality of line segments before the reaction segment having a slope not more than a flatness criteria;

d) fitting a line segment to data points associated with the baseline region to form a baseline segment; and e) extending the baseline segment to form a baseline.

17. The method of claim 16 wherein the flatness criteria is calculated with the following formula:

$$\text{flatness criteria} = \mu - C_1 \times \sigma$$

wherein $\mu$ is the average absolute slope of all the line segments, $C_1$ is a flatness constant, and $\sigma$ is the standard deviation of the absolute slopes of all of the line segments.

18. The method of claim 17 wherein $C_1 = 0.5$.

19. The method of claim 16 wherein identifying the baseline of the PCR amplification reaction further comprises:
subtracting the product values for the baseline from the data points.

20. The method of claim 1 wherein the steepness criteria is calculated with the following formula:

$$\text{steepness criteria} = \mu + C_2 \times \sigma$$

wherein $\mu$ is the average absolute slope of all of the line segments, $C_2$ is a steepness constant, and $\sigma$ is the standard deviation of the absolute slopes of all of the line segments.

21. The method of claim 20 wherein $C_2 = 0.65$.

22. The method of claim 1 wherein the exponential region further includes one data point before the subset of the plurality of line segments having the slope not less than the steepness criteria and one data point after the subset of the plurality of line segments having the slope not less than the steepness criteria.

23. A computer program product comprising:
a non-transitory computer readable medium; and
program instructions for performing the method of claim 1, wherein the program instructions are stored on the non-transitory computer readable medium.

24. A method of generating a combined quantitation cycle ($C_q$) for a plurality of Polymerase Chain Reaction (PCR) amplification reactions, characterized by a plurality of data points each including a cycle value associated with a PCR cycle and a product value associated with a PCR product, the method comprising:
identifying, using a processor, an individual $C_q$ for each of the plurality of PCR amplification reactions and averaging the individual $C_q$s to obtain a combined $C_q$,
wherein the individual $C_q$ for each of the plurality of PCR amplification reactions is identified by performing the steps comprising:
a) fitting a plurality of line segments to the data points associated with the PCR amplification reaction;
b) identifying a baseline of the PCR amplification reaction;
c) identifying a reaction segment associated with an exponential region of the PCR amplification reaction as a first subset of the plurality of line segments having a slope not less than a steepness criteria;
d) fitting a reaction line to the data points associated with the reaction segment; and
e) extrapolating the reaction line to intersect the baseline at the $C_q$.

25. A system for identifying a quantitation cycle ($C_q$) for a Polymerase Chain Reaction (PCR) amplification reaction characterized by a plurality of data points each including a cycle value associated with a PCR cycle and a product value associated with a PCR product, the system comprising:
a data analysis module, the data analysis module being configured to:
a) fit a plurality of line segments to the data points associated with the PCR amplification reaction;
b) identify a baseline of the PCR amplification reaction;
c) identify a reaction segment associated with an exponential region of the PCR amplification reaction as a first subset of the plurality of line segments having a slope not less than a steepness criteria;
d) fit a reaction line to the data points associated with the reaction segment; and
e) extrapolate the reaction line to intersect the baseline at the $C_q$.

26. The system of claim 25 further comprising a data collection module, the data collection module configured to receive data points from at least one PCR amplification reaction.

27. A method of identifying a baseline of a Polymerase Chain Reaction (PCR) amplification reaction comprising:
a) identifying, using a processor, a baseline region associated with the PCR amplification reaction wherein the baseline region includes the longest consecutive subset of the plurality of line segments before the reaction segment having a slope not more than a flatness criteria;
d) fitting a line segment to data points associated with the baseline region to form a baseline segment; and
e) extending the baseline segment to form a baseline.

28. The method of claim 27 wherein the flatness criteria is calculated with the following formula:

$$\text{flatness criteria} = \mu - C_1 \times \sigma$$

wherein $\mu$ is the average absolute slope of all the line segments, $C_1$ is a flatness constant, and $\sigma$ is the standard deviation of the absolute slopes of all of the line segments.

29. The method of claim 28 wherein $C_1 = 0.5$.

30. The method of claim 27 wherein identifying the baseline of the PCR amplification reaction further comprises:
subtracting the product values for the baseline from the data points.

* * * * *